United States Patent [19]

Georgaras et al.

[11] Patent Number: 5,235,441
[45] Date of Patent: Aug. 10, 1993

[54] HOLOGRAPHIC LENSES

[76] Inventors: Spyros Georgaras; Chris Tripos, both of 13, I. Metaxa St., 16675 Glyphada, Greece

[21] Appl. No.: 897,073

[22] Filed: Jun. 11, 1992

Related U.S. Application Data

[63] Continuation-in-part of Ser. No. 701,593, May 13, 1991, abandoned, which is a continuation of Ser. No. 362,210, Jun. 6, 1989, abandoned.

[51] Int. Cl.$^5$ .................. G02B 5/32; G02C 7/02; G03H 1/04
[52] U.S. Cl. .................. 359/15; 351/159; 351/177; 359/19
[58] Field of Search .................. 359/15, 19, 22, 24; 351/159, 177; 264/1.3

[56] References Cited

U.S. PATENT DOCUMENTS

| | | | |
|---|---|---|---|
| 4,601,533 | 7/1986 | Moss | 359/24 |
| 4,641,934 | 2/1987 | Freeman | 359/19 |
| 4,830,441 | 5/1989 | Chane | 359/24 |

FOREIGN PATENT DOCUMENTS 2101764  1/1983  United Kingdom .................. 359/19

*Primary Examiner*—Martin Lerner
*Attorney, Agent, or Firm*—Kane, Dalsimer, Sullivan, Kurucz, Levy, Eisele and Richard

[57] ABSTRACT

A method of constructing holographic lenses for correction of a person's deficiencies comprises splitting a filtered laser beam onto an object under consideration and thence to a photographic film, and simultaneously conducting the other beam to the film as a reference whereby the interference patterns between the two beams form a hologram which is developed by ordinary photographic process. The hologram can be visualized by the user of the lens when the reference beam is conducted to the developed film. The lenses are individualized to correct for the particular optical deficiencies of a user by varying the focal distance.

6 Claims, 3 Drawing Sheets

HOLOGRAPHIC LENSES

This application is a continuation-in-part of application Ser. No. 07/701,593, filed on May 13, 1991 now abandoned which is a continuation of application Ser. No. 07/362,210, filed on Jun. 6, 1989 now abandoned.

BACKGROUND OF THE INVENTION

1. Field of the Invention

The present invention relates to holographic lenses for eyesight correction and to a method for creating such lenses.

2. Description of the Prior Art

For the purposes of this application, holography can generally be defined as a lenseless photographic method that uses laser light to produce 3-dimensional images by splitting the laser beam into two beams and recording on a photographic surface the minute interference patterns made by the reference light waves which may be reflected from a mirror and the waves modulated when simultaneously reflected from the object. The virtual image can be reconstructed by shining laser light, white light, etc. through the developed film.

A method of recording and reproducing wave fronts was proposed by D. Gabor in the publication "NATURE" 161 777 (1948) for use in microscopy.

The subsequent development of laser technology resulted in a whole new branch of optic science being formed which was named holography. Holography is based on the recording of the mutual interference of two coherent optical waves originating from the same laser source on a photosensitive material. The interference requires two beams: the reference beam which is usually a plane parallel wave of constant amplitude and phase, and the object beam which is light scattered from the object to be recorded and therefore carries amplitude and phase information related to it. This mutual interference of a coherent reference beam and a coherent object beam results in not only the recording of the average intensity (as in ordinary photography) but also the phase of the waves. Thus the hologram holds all the information relative to the object beam and can reproduce it as well.

In prior art processes the hologram recording is processed by chemical means as in ordinary photography. The process material is illuminated by the reference beam used during the recording, its diffraction reproduces exactly the recorded object beam.

Other prior art publications which are relevant to the present invention include "HOLOGRAPHIE" by M. Francon, published by Masson & Cie (1969); "OPTICAL INFORMATION PROCESSING AND HOLOGRAPHY" by W. T. Cathey, published by J. Wiley (1974); and "OPTICS" by M. B. Klein, published by J. Wiley (1970).

OBJECTIVES AND SUMMARY OF THE INVENTION

The primary objective of the present invention is the production of holographic lenses on photographic film or any dioptric power in the use for the correction of ametropia. Ametropia is a generic term which refers to any condition of imperfect refraction of the eyes such as nearsightedness, far sightedness, or astigmatism.

This and other objects of the invention are achieved as explained in the following summary.

In the present invention a hologram is achieved by recording the interference of two optical fields, the reference field which is a parallel monochromatic laser He-Ne beam and the object field or beam which emanates from the same source (i.e. coherent). The result is a convergent beam representing a convergent angle of the lenses whose hologram is being produced. Thus it can be sen that the hologram effectively is a lens.

The holographic lens of the present invention is produced in accordance with the optical needs of the user. Thus a specific hologram is produced on the photosensitive film for each user such that the focal distance is appropriate for that user.

An important advantage of the holographic lenses is produced by the method of the present invention which is not found in ordinary eyeglass lenses is that the holographic lenses are extremely light and of uniform thickness regardless of whatever dioptric power is produced by the hologram. Also, they can be produced using a simple photographic process rather than the complicated industrial processes used in shaping the curvature of ordinary eyeglass lenses.

DESCRIPTION OF THE PREFERRED EMBODIMENT

Figure 1A:
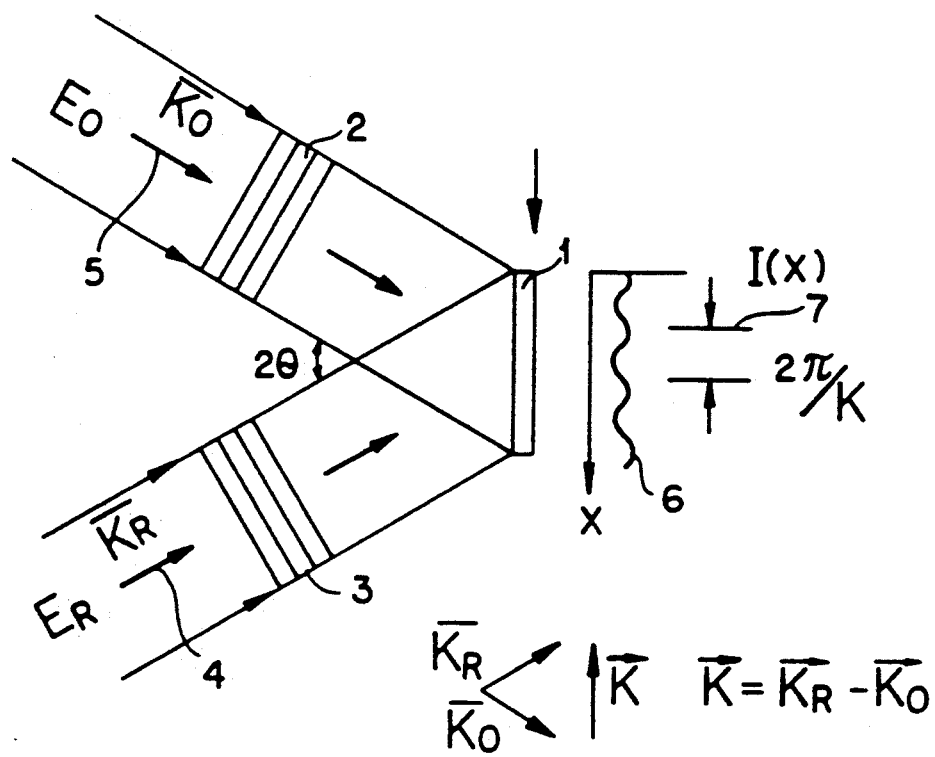
FIG. 1A is a schematic showing the prior art general holographic method wherein an object beam and reference beam combine to form a hologram.

In the prior art method shown in FIG. 1, an object beam 5 is conducted through a diffraction grating to a photosensitive surface such as a film lens. Simultaneously, another coherent laser generated beam 4 which is designated as a reference beam is directed through diffraction grating to photosensitive surface 1. The interaction between the two coherent beams 4 and 5 results in hologram being produced on photosensitive surface 1.

Assuming a wave length $\lambda$ for the two coherent beams of monochromatic light, the mathematics for generation of a hologram for two flat waves of the following forms are as follows:

$$\begin{bmatrix} Ep = /Ap/ \exp(-i\ Kp\ r) \\ Eo = /Ao/ \exp(-i\ Ko\ r) \end{bmatrix}$$

with wave vectors Kr, Ko where they $$/Ko/ = /Kr/ = 2\pi/\lambda$$

the angle between Kr and Ko = 2* θ illuminate the photosensitive material.
(* complex conjugate)

The intensity of the interaction field will be:

I(p) is proportional to
(Ep+Eo)·(Ep+Eo)* = /Ar/² + /Ao/² + 2 /Ar/ /Ao/ cos (K−r)

where
K = Kr − Ko and
r = position vector

The material's transmission function T will be proportional to:

[I(p)]** (−Y/2)

and will also be proportional to any of the following two functions:

$$2[/Ao/^2 - Y/2/Ar/^2 - Y/Ao/ /Ap/\cos (K - r)]$$

$$B - Y/2 /Ao/ /Ar/ [\exp(i K^*r) + \exp(-i K^*r)]$$

after development of the plate.

Figure 1B:
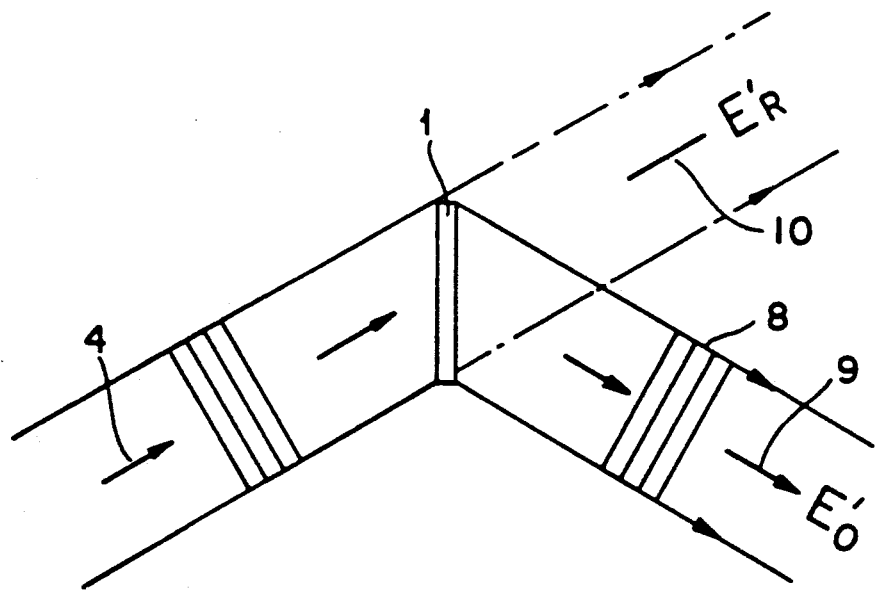
FIG. 1B shows a reproduction of the object beam of FIG. 1A after a film on which the hologram has been recorded is illuminated with the reference beam.

As shown in FIG. 1B, the photosensitive film lens having the hologram imprinted therein is illuminated by the reference B $E^R$. The diffracted fields which is sent to the eye of the viewer coming from a second useful term of the previous equation would be of the form:

Eo' is proportional to Y/2 /AP/² /Ao/
exp(−iKo−r)

which is relative to the object's beam.

Figure 2A:
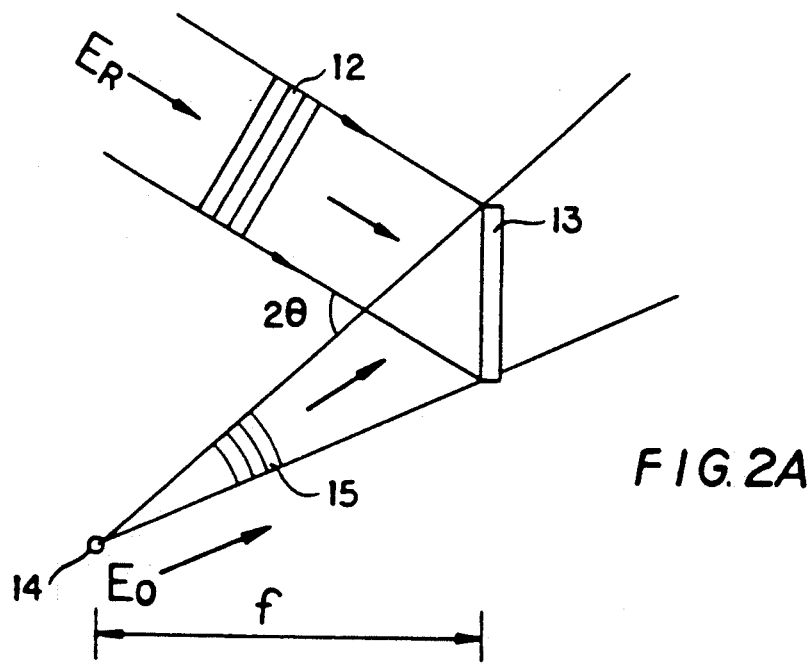
FIG. 2A weighs a schematic of a hologram produced by a reference beam and an object beam wherein the object beam is a divergent or convergent spherical weight (as if coming from a single point light source at a distance of f from the recording material).
Figure 2B:
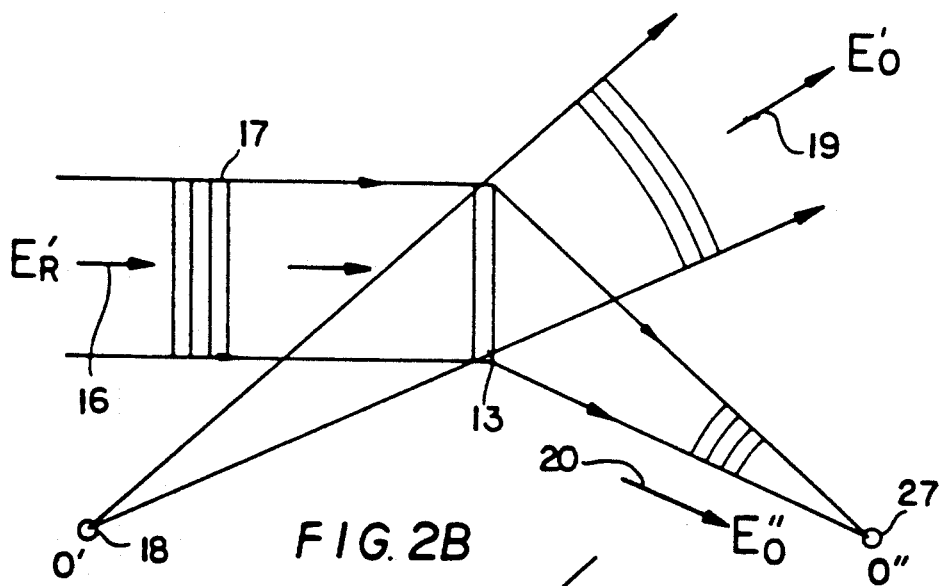
FIG. 2B shows a schematic of a reproduction of the object beam of FIG. 2A produced when the photosensitive material is illuminated with the reference beam.
Figure 2C:
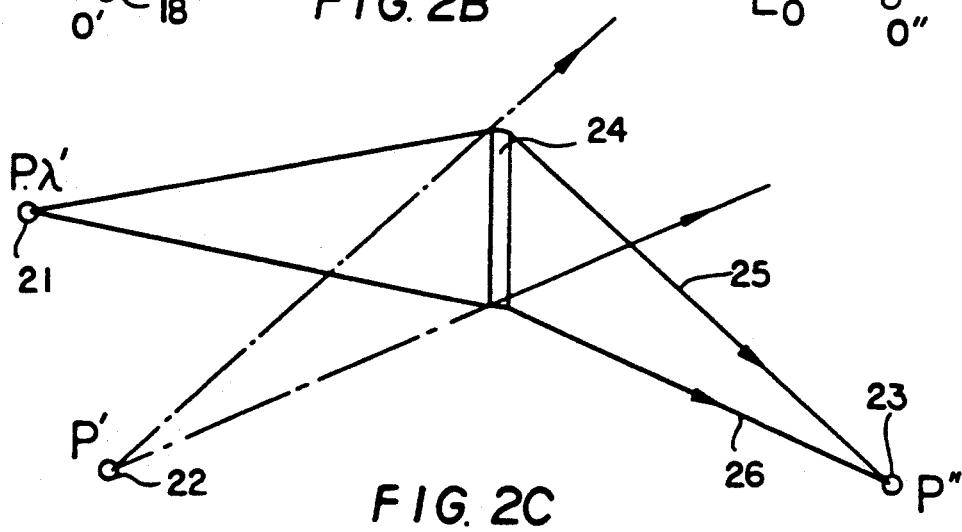
FIG. 2C is a schematic of a single slant light source illuminating the photosensitive material at a specific wave length.

FIGS. 2A–2C show the generation of a hologram when the object beam used for recording is a divergent or convergent spherical wave which can be viewed as of coming from a single point light source which is f distance from the photosensitive material. Thus, as shown in FIG. 2A, a point source object beam 14 (E₀) passes through a diffraction grating 15 to impinge on a photosensitive surface 13. Simultaneously another coherent laser generated reference beam 11 (E_R) passes through diffraction grating 12 to impinge on photosensitive surface 13. As shown in the Figure, the object point source is located at a distance f from the photosensitive material.

FIG. 2B shows the reproduction of a hologram for conveying it to the eye of a viewer by using a reference coherent light beam 16 which passes through diffraction grating 17 to impinge on the holograph containing photosensitive surface 13 and a divergent or convergent object beam 18 which reproduces object beams 19 (E' and E'') with object beam 19 being divergent and object beam 20 being convergent on converging at point 27 (O'').

FIG. 2C is similar to FIG. 2B and uses a wave length ' for its reference beam 21 which together with the object coherent light beam 22 imprints a hologram on photographic surface 24 which both diverges and converges with the convergent beam converging at point 23 (P'').

Figure 3:
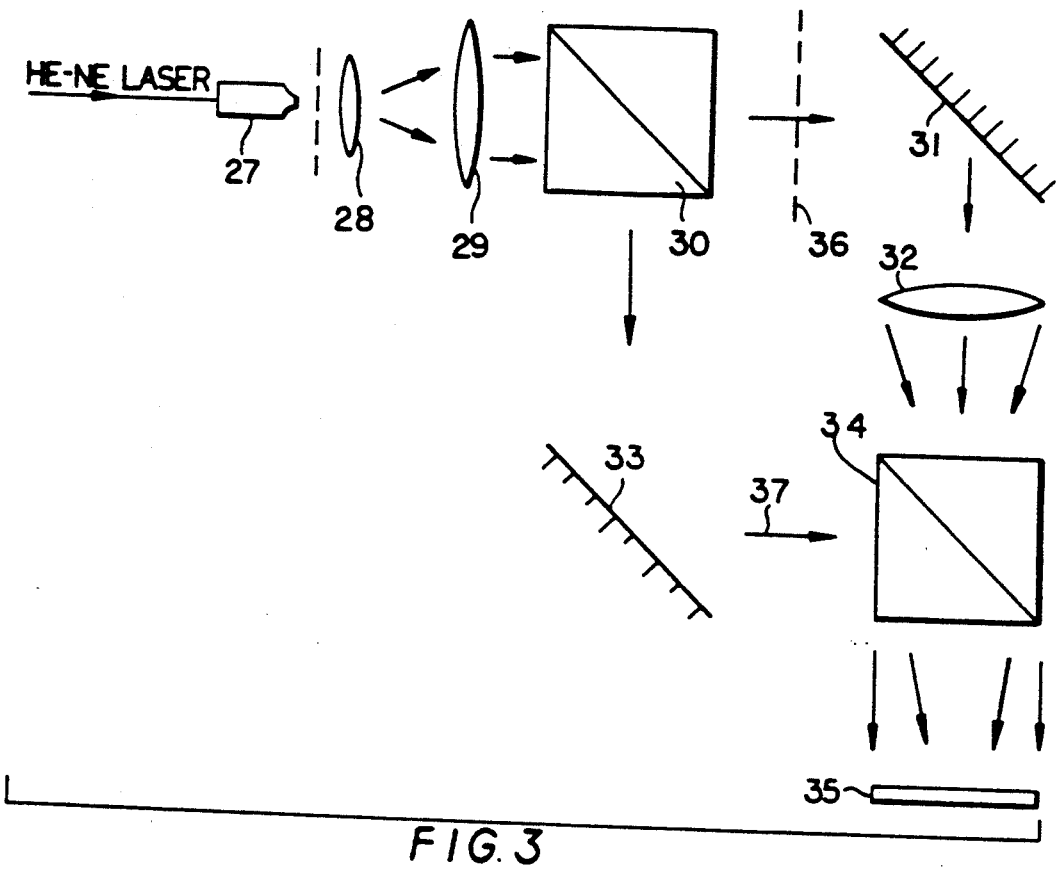
FIG. 3 is a schematic showing in detail how a hologram is produced on a lens for a user's specific optical requirement according to the method of the present invention.

The method of the present invention is illustrated in FIG. 3 wherein a helium-neon laser beam (λ = 1.638 μm) is photographed and enlarged by lenses 28 and 29.

The beam then gets divided by beam splitter 30 and then passes through diffraction grating 36 to impinges upon reflector 31(A) wherefrom it is directed the object 32 and beam splitter 34 to finally impinge upon a photosensitive film 35. Simultaneously the other portion of the beam which was split by beam splitter 34 whereupon it is finally conducted to photosensitive surface or film 35. Thus a hologram is produced upon film 35 which, upon being illuminated by the reference beam 37 can produce a holographic image which is conducted to the eye of the viewer. As stated previously, an essential feature of the invention is that the focal length is adjusted to meet the optical requirements of each individual.

Figure 4:
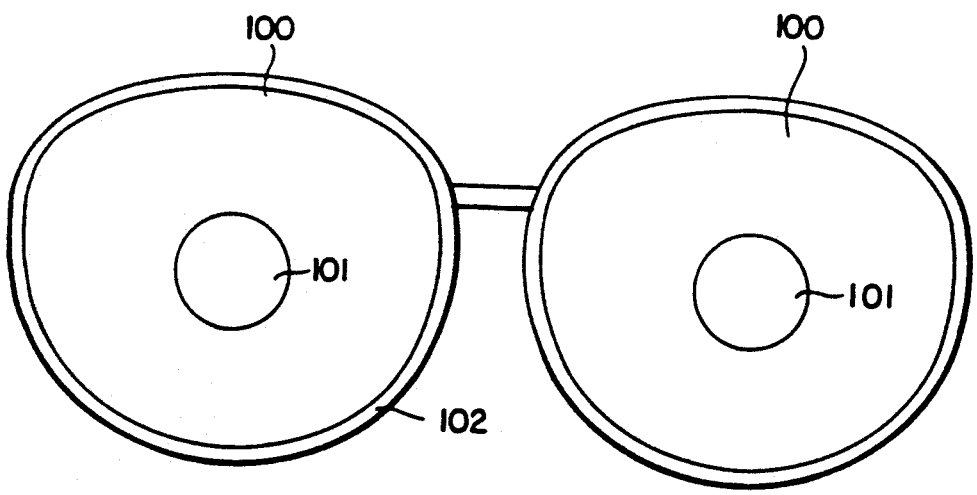
FIG. 4 is a plan view of the lens on an eyeglass frame.

As shown in FIG. 4 the resulting lens 100 will typically include a refractory area 101 which is typically 1–4 centimeters in diameter and therefore will not subtend the entire diameter of an eyeglass frame 102.

Additionally, the resulting lens will refract a portion of the light positively, a portion negatively, and allow the remaining portion to pass through unrefracted. The user's eye will focus upon the most coherent or sensible image available to it.

Among the advantages of the use of a holographic lens for eyeglasses is the fact that its resolution is very high theoretically can reach 1000 lines/mm. independently of the lenses' diameter.

In constructing the holographic lenses of the present invention, an exposure of 20 μJ/cm was used. The resulting holographic films were transformed into phase holograms so as to increase diffraction.

Although a preferred embodiment of the invention has been shown herein, it is clear that many variations of the invention can be practiced within the scope of the appended claims.

We claim:
1. A method of making flat holographic eyeglass lenses for the correction of a user's ametropia comprising the steps of:
   determining an appropriate focal distance for said correction of ametropia;
   then simultaneously reflecting a first coherent light beam as an object beam onto a flat photographic film and a second coherent light beam onto said film whereby a hologram is produced having said appropriate focal distance and
   developing the film by ordinary photographic process thereby creating a lens with a refractory area with a diameter of one to four centimeters, which is free from subtending the entire portion of the eyeglass lens.

2. The method of claim 1 wherein said first and second coherent light beams are generated by a single laser having an output into a beam splitter from which said first and second coherent light beams emanate.

3. The method of claim 1 wherein said first coherent light beam reflected from said object is a convergent spherical wave.

4. The method of claim 1 wherein said first coherent light beam reflected from said object is a divergent spherical wave such that it appears to be a single joint light source at a certain distance from the film.

5. The method of claim 1 further comprising the step of shining said second coherent light beam on said developed film whereby a focused image of the hologram is produced at the user's eye.

6. A holographic lens produced by the method of claim 1.

* * * * *